(12) United States Patent
Bowdon et al.

(10) Patent No.: US 9,897,558 B2
(45) Date of Patent: Feb. 20, 2018

(54) SCANNING METHOD AND APPARATUS

(71) Applicants: JOHNSON MATTHEY PUBLIC LIMITED COMPANY, London (GB); Kenneth Pearson, Floreat (AU)

(72) Inventors: Christopher Bowdon, Kempston (GB); Paul David Featonby, Wylam (GB); James Stephen Howstan, Bishop Auckland County (GB); Peter Jackson, London (GB); Kenneth James, Cleveland (GB); Emanuele Ronchi, Cleveland (GB)

(73) Assignee: JOHNSON MATTHEY PUBLIC LIMITED COMPANY, London (GB)

( * ) Notice: Subject to any disclaimer, the term of this patent is extended or adjusted under 35 U.S.C. 154(b) by 372 days.

(21) Appl. No.: 14/355,268

(22) PCT Filed: Nov. 2, 2012

(86) PCT No.: PCT/GB2012/052737
§ 371 (c)(1),
(2) Date: Apr. 30, 2014

(87) PCT Pub. No.: WO2013/064838
PCT Pub. Date: May 10, 2013

(65) Prior Publication Data
US 2015/0241572 A1    Aug. 27, 2015

Related U.S. Application Data

(60) Provisional application No. 61/597,354, filed on Feb. 10, 2012, provisional application No. 61/597,237, (Continued)

(30) Foreign Application Priority Data

Nov. 2, 2011  (GB) .................................. 1118943.8
Nov. 2, 2011  (GB) .................................. 1118944.6
Jan. 17, 2012  (GB) .................................. 1200744.9

(51) Int. Cl.
*G01N 23/04*   (2006.01)
*G01T 1/20*    (2006.01)
(Continued)

(52) U.S. Cl.
CPC ............ *G01N 23/046* (2013.01); *G01N 9/24* (2013.01); *G01T 1/164* (2013.01); *G01T 1/2018* (2013.01); *G21K 1/02* (2013.01); *G01N 2223/419* (2013.01)

(58) Field of Classification Search
CPC ............ G01N 23/046; G01N 2223/419; G01T 1/2018
(Continued)

(56) References Cited

U.S. PATENT DOCUMENTS 3,922,833 A    12/1975  Eaton
4,284,895 A    8/1981   Morgan et al.
(Continued)

FOREIGN PATENT DOCUMENTS

CN    1481510 A      3/2004
CN    101535835 A    9/2009
(Continued)

OTHER PUBLICATIONS

GB Search report, dated Sep. 21, 2015; Application No. GB1515011.3.
(Continued)

*Primary Examiner* — Allen C. Ho
(74) *Attorney, Agent, or Firm* — Young & Thompson

(57) ABSTRACT

The invention discloses a scanning method and apparatus suitable for scanning a pipeline or process vessel in which a beam of gamma radiation from a source is emitted through the vessel to be detected by an array of detectors which are each collimated to detect radiation over a narrow angle relative to the width of the emitted radiation beam.

17 Claims, 8 Drawing Sheets

Related U.S. Application Data filed on Feb. 10, 2012, provisional application No. 61/597,272, filed on Feb. 10, 2012.

(51) Int. Cl.
*G21K 1/02* (2006.01)
*G01T 1/164* (2006.01)
*G01N 9/24* (2006.01)

(58) Field of Classification Search
USPC ............... 378/19, 51, 53, 54, 57, 98.8, 146;
250/363.01, 363.02, 363.03, 363.04,
250/370.09
See application file for complete search history.

(56) References Cited

U.S. PATENT DOCUMENTS

| | | | |
|---|---|---|---|
| 4,338,521 A | 7/1982 | Shaw et al. | |
| 4,422,177 A * | 12/1983 | Mastronardi | A61B 6/0457 378/10 |
| 4,700,074 A | 10/1987 | Bosnjakovic | |
| 4,725,963 A | 2/1988 | Taylor et al. | |
| 4,989,225 A * | 1/1991 | Gupta | G01N 23/046 378/10 |
| 5,030,830 A | 7/1991 | Okada | |
| 5,144,141 A * | 9/1992 | Rougeot | G01T 1/2018 250/366 |
| 5,166,961 A | 11/1992 | Brunnett et al. | |
| 5,313,513 A * | 5/1994 | Prindiville | G01N 23/046 378/20 |
| 5,378,894 A | 1/1995 | Akai | |
| 5,379,237 A * | 1/1995 | Morgan | B21B 37/78 378/59 |
| 5,614,720 A | 3/1997 | Morgan et al. | |
| 5,668,851 A | 9/1997 | Dobbs | |
| 5,773,829 A * | 6/1998 | Iwanczyk | G01T 1/1644 250/367 |
| 6,087,663 A * | 7/2000 | Moisan | G01T 1/2002 250/367 |
| 6,365,900 B1 * | 4/2002 | Mestais | G01T 1/1642 250/363.1 |
| 6,377,654 B1 | 4/2002 | Willems et al. | |
| 6,519,313 B2 * | 2/2003 | Venkataramani | G01T 1/2018 250/367 |
| 6,717,150 B2 * | 4/2004 | Hoffman | G01T 1/2018 250/367 |
| 6,822,240 B2 | 11/2004 | Francke et al. | |
| 6,907,101 B2 * | 6/2005 | Hoffman | G01T 1/2985 250/370.09 |
| 6,925,145 B2 * | 8/2005 | Batzinger | G01N 23/18 378/4 |
| 6,934,354 B2 * | 8/2005 | Hoffman | A61B 6/032 378/149 |
| 7,164,136 B2 * | 1/2007 | Aykac | G01T 1/1644 250/366 |
| 7,235,790 B2 * | 6/2007 | Hoge | G01T 1/1648 250/370.09 |
| 7,286,630 B2 * | 10/2007 | Holt | A61B 6/032 378/20 |
| 7,329,875 B2 * | 2/2008 | McEvoy | G01T 1/2018 250/367 |
| 7,375,337 B2 * | 5/2008 | Gagnon | A61B 6/037 250/363.05 |
| 7,408,164 B2 * | 8/2008 | Schmand | G01T 1/202 250/361 R |
| 7,410,606 B2 * | 8/2008 | Appleby | B23P 15/246 249/117 |
| 7,504,635 B2 * | 3/2009 | Ramsden | G01T 1/1642 250/369 |
| 7,535,008 B2 * | 5/2009 | Tsuchiya | G01T 1/2928 250/363.1 |
| 7,544,927 B1 | 6/2009 | Iwatschenko-Borho | |
| 7,791,030 B2 * | 9/2010 | Tonami | G01T 1/1644 250/363.05 |
| 7,885,381 B2 * | 2/2011 | Nagumo | G01B 15/025 378/41 |
| 7,928,396 B2 * | 4/2011 | Soluri | G01T 1/1644 250/361 R |
| 7,939,807 B2 * | 5/2011 | Soluri | G01T 1/1644 250/369 |
| 8,188,439 B2 * | 5/2012 | Gagnon | G01T 1/202 250/366 |
| 8,306,182 B2 * | 11/2012 | Yaoi | A61B 6/035 250/370.09 |
| 8,391,439 B2 * | 3/2013 | Levene | G01T 1/2018 250/370.09 |
| 8,426,823 B2 * | 4/2013 | Schulz | G01T 1/2002 250/368 |
| 8,483,362 B2 * | 7/2013 | Freund | G21K 1/025 378/147 |
| 8,536,552 B2 * | 9/2013 | Freund | G01T 1/1648 250/370.09 |
| 8,552,388 B2 * | 10/2013 | Wirth | G01T 1/2985 250/363.04 |
| 8,569,707 B2 * | 10/2013 | Watanabe | G01T 1/2928 250/369 |
| 8,761,333 B2 * | 6/2014 | Ikhlef | A61B 6/032 29/428 |
| 8,798,229 B2 * | 8/2014 | Li | A61B 6/032 250/370.09 |
| 8,809,790 B2 * | 8/2014 | Woldemichael | G01T 1/2985 250/362 |
| 8,822,931 B2 * | 9/2014 | Laurence | G01T 1/1644 250/362 |
| 8,842,809 B2 * | 9/2014 | Samant | G01T 1/20 378/154 |
| 9,020,093 B2 * | 4/2015 | Kurochi | G21K 1/025 378/18 |
| 9,035,259 B2 * | 5/2015 | Featonby | G01F 23/288 250/357.1 |
| 9,063,237 B2 * | 6/2015 | Valentino | G01T 1/1642 |
| 9,263,160 B2 * | 2/2016 | Kang | G21K 1/025 |
| 9,380,987 B2 * | 7/2016 | Kojima | G01T 1/2002 |
| 9,488,604 B2 * | 11/2016 | Wuestenbecker | G01N 23/18 |
| 2002/0070343 A1 | 6/2002 | Hoffman | |
| 2002/0074505 A1 | 6/2002 | Francke et al. | |
| 2002/0181647 A1 | 12/2002 | Venkataramani et al. | |
| 2004/0174951 A1 | 9/2004 | Hoffman | |
| 2004/0218713 A1 | 11/2004 | Hoffman | |
| 2007/0086565 A1 | 4/2007 | Thompson et al. | |
| 2009/0127449 A1 | 5/2009 | Iwatschenko-Borho | |
| 2011/0114845 A1 | 5/2011 | Gagnon et al. | |
| 2011/0220800 A1 | 9/2011 | Featonby et al. | |
| 2015/0219485 A1 | 8/2015 | Featonby et al. | |

FOREIGN PATENT DOCUMENTS

| | | |
|---|---|---|
| CN | 101634712 A | 1/2010 |
| DE | 2642064 | 3/1978 |
| EP | 3039916 A1 | 11/1981 |
| FR | 2 455 292 | 11/1980 |
| JP | 62-277943 A | 12/1987 |
| JP | 2-206792 A | 8/1990 |
| JP | 2003-130819 | 5/2003 |
| WO | 99/30615 | 6/1999 |
| WO | 2010005977 A2 | 1/2010 |
| WO | 2010-032064 | 3/2010 |

OTHER PUBLICATIONS

GB Search report, dated Sep. 21, 2015; Application No. GB1515013.9.
International Search Report dated Jan. 23, 2013, corresponding to PCT/GB2012/052737.
British Search Report dated Mar. 14, 2013, corresponding to the Foreign Priority Application No. GB1219790.1.

(56) References Cited

OTHER PUBLICATIONS

Bieberle, et al.; "Design of High-Resolution Gamma-Ray Detector Module for Tomography Applications"; vol. 572, No. 2; Feb. 14, 2007; pp. 668-675.

G.A. Johansen, et al.; "Gamma Detectors for Tomographic Flow Imaging"; vol. 5, No. 1; Jan. 1, 1994; pp. 15-21.

U. Hampel, et al.; High Resolution Gamma Ray Tomography Scanner for Flow Measurement and Non-Destructive Testing Applications; vol. 78, No. 10; Oct. 12, 2007; pp. 103704-103704.

English translation of Japanese Examination Report, dated Aug. 23, 2016, corresponding to Japanese Patent Application No. 2014-539407.

English translation of Chinese Examination Report, dated Oct. 29, 2015, corresponding to Chinese Patent Application No. 201280062513.4.

UK Search Report, dated Feb. 22, 2012, corresponding to British Patent Application No. GB1118944.6.

* cited by examiner

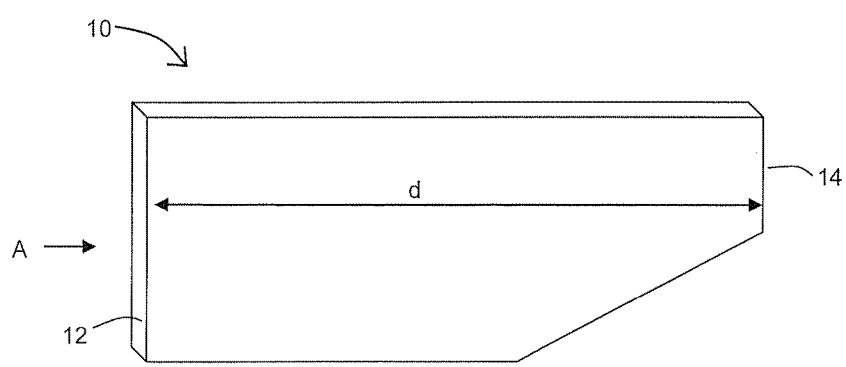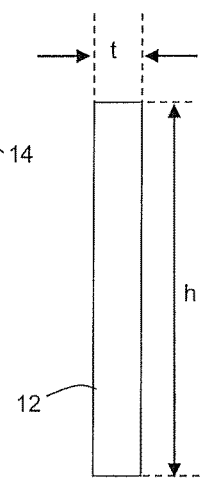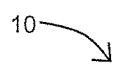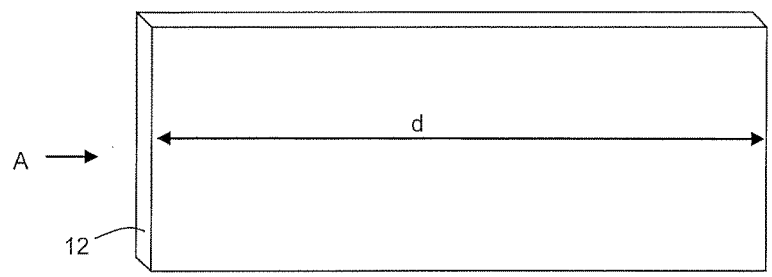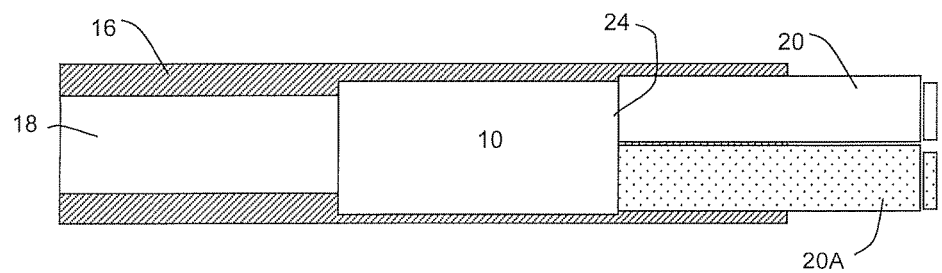

SCANNING METHOD AND APPARATUS

BACKGROUND OF THE INVENTION

Field of the Invention

The present invention relates to a method of scanning a structure to detect changes in density by means of detecting radiation emitted by a radiation source by a radiation detector.

DESCRIPTION OF THE RELATED ART

Methods of imaging objects and animals by X-ray tomography and positron-emission tomography are well-known, particularly in the field of medical imaging for diagnostic purposes. U.S. Pat. No. 4,338,521 describes an X-ray scanner for use in computerised tomography which has a detector comprising an array of detector modules, comprising a plurality of photodiodes and a plurality of scintillator crystals and a radiation beam collimator to direct collimated radiation to the scintillator crystals. A fan-shaped beam of x-rays from an x-ray source is directed through a patient to be detected by the detector. The source and detector are rotated around the patient to provide the data from which a tomographic image may be constructed. In positron-emission tomography (PET) a positron emitted by the decay of a radionuclide annihilates on contact with a suitable electron, causing the emission of two gamma photons of 511 keV in opposite directions. The detection of the direction of the gamma photons enables the estimation of the location of the annihilation event and thus the radionuclide within the patient. The PET scanner therefore incorporates an array of detectors which can detect gamma photons placed around the body of a patient. An image of the relative concentration of the radionuclide in the body may be constructed from the number of photons detected at each detector.

Whilst these scanning methods are well-developed and have become common for medical scanning, scanning a dense structure such as a pipeline presents difficulties because the density of the pipeline material is such that radiographic scanning must be done using gamma radiation which is of sufficient energy to penetrate and pass through the structure so that at least some radiation can be detected after the beam has passed through the structure. Gamma scanning of structures such as distillation columns is a standard industrial diagnostic method for measuring changes in density at different parts of the structure, for example to determine the location and integrity of column trays or other internal structures within the column. Normally this type of scanning is carried out with a single gamma source placed adjacent the column to emit a beam of radiation through the column and a radiation detector placed on an opposed part of the column to intersect and measure the radiation that has traversed the column between the source and detector. The source and detector are normally moved so that different parts of the column can be scanned. The use of many different positions and more than one source or detector can provide sufficient data for generating density maps, or tomographs, of the structure which is scanned, although the resolution is generally quite coarse. In order to generate higher resolution density maps, information from a much larger number of radiation paths through the structure must be used than is currently achieved with conventional column scanning methods.

The inspection of pipelines to find flaws such as wall loss, cracks or corrosion pitting is an application in which it would be desirable to use radiation scanning. A known problem for the oil and gas production industry is the inspection of pipelines located underwater, in particular on the sea-bed. Inspection of the interior of the pipeline by the use of pigs is not always possible, for example when the pipeline has varying diameter. Inspection from outside the pipe may be carried out by ultrasonic methods, although this is not suitable for pipelines having an insulation or coating. Gamma scanning can produce useful information about the density through a cross-section of the pipe. In order to produce information about the thickness of the walls of the pipe at sufficiently high resolution to identify small flaws that may be present in the walls of the pipe a large number of radiation paths through the pipe need to be scanned. Furthermore, if a fan-shaped radiation beam is to be used to scan the pipe, many of the radiation paths pass through a chord of the pipe cross-section and therefore through a relatively large amount of the pipeline wall material, requiring a relatively high energy gamma source. In order to detect the gamma radiation that has passed through the structure it is necessary to use detectors of sufficient size and density to stop the gamma photons so they do not pass through the detector undetected. In order to maintain a high resolution the collimation of the detectors has to be sufficient to significantly reduce detection of gamma photons which have been scattered from a path other than the direct path to a particular detector. The detectors need to be small enough to provide good spatial resolution. A large number of detectors is needed to achieve a reasonable measurement time. The use of heavy collimation on a large number of detectors necessitates a scanning apparatus which is very heavy and so rotation of the apparatus in a controlled and precise manner around a large pipeline becomes very difficult. When the pipeline is horizontal, it becomes necessary to trench the pipe in order to allow sufficient space in which to move a scanning apparatus and so the use of large apparatus becomes expensive, particularly when the pipeline is located sub-sea. All of these considerations bring particular problems to the application of high resolution x-ray tomography methods to the scanning of pipelines or other large structures with high energy gamma radiation.

BRIEF SUMMARY OF THE INVENTION

It is an object of the present invention to provide such a method, although the method of the invention may be useful for scanning structures other than pipelines and for use in locations including both dry and sub-sea locations.

The present invention relates to a method of scanning a structure to detect its physical properties. In particular the invention relates to a method of scanning an elongate structure, such as a pipeline, to detect changes in its material density which may indicate variations in wall thickness caused by corrosion or erosion or to deduce information about the contents of the pipeline such as the build-up of deposits or the nature of fluid flowing within the pipeline. Typically, the method and apparatus concerns the measurement of density of a structure by means of detecting radiation emitted by a radiation source by a radiation detector.

According to the invention, we provide a method of scanning a structure to detect changes in density between different parts of the structure comprising the steps of:
  a) providing at least one source of gamma radiation, and
    a plurality of detector units capable of detecting said gamma radiation, each said detector unit comprising:
      i. a radiation detector comprising a scintillator comprising a scintillating material and having a detecting surface defined by its thickness t and height h, wherein t≤h at the detecting surface and having a depth d perpendicular to the detecting surface at least 2t, and ii. a photodetector for detecting light emitted by the scintillator in response to gamma radiation, and iii. a collimator placed between the scintillator and the source of radiation;

b) causing said source to emit gamma radiation along a predetermined radiation path towards said detector, wherein said path passes through at least a portion of said structure;

c) measuring the number of photons of gamma radiation detected by each one of said detectors;

d) calculating a density value for each path from the measurement of photons detected by the detector associated with the respective path.

According to the invention, we provide an apparatus for scanning a structure to detect changes in density between different parts of the structure comprising:

at least one source unit comprising a source of gamma radiation and shielding material arranged to restrict the emission of gamma radiation from the source unit: a plurality of detector units capable of detecting said gamma radiation, each said detector unit comprising:

i. a radiation detector comprising a scintillator comprising a scintillating material and having a detecting surface defined by its thickness t and height h, wherein t≤h at the detecting surface and having a depth d perpendicular to the detecting surface at least 2t, and ii. a photodetector for detecting light emitted by the scintillator in response to gamma radiation, and iii. a collimator placed between the scintillator and the source of radiation;

and data processing means for calculating a density value for each path from the measurement of photons detected by the detector associated with the respective path.

The apparatus of the invention is suitable for use in the scanning method of the invention, in which a target structure is scanned to detect changes in its shape or composition by means of passing radiation emitted by a radiation source through the structure and detecting radiation after it has passed through the structure. The method works on the well-known principle that the amount of radiation attenuated or scattered by an object is related to the mass of material the radiation has passed through. By measuring the amount of radiation detected through each selected path through the target structure it is possible to calculate and/or compare the density of the structure along one radiation path with the density of the structure along a different radiation path. By "density value" we mean a value which represents the actual or relative density of the structure which lies on a particular path from the source to a particular detector. The density value may take the form of a number of counts of gamma photons or a normalised, smoothed or comparative number of counts of gamma photons. Alternatively the density value may be a value calculated from the number of counts of gamma photons. The density value may be expressed graphically, including as an image or part thereof. The relative dimensions of the scintillator(s) of the radiation detector of the invention allow a plurality of scintillators to be placed in close proximity in order to achieve a high degree of spatial resolution of detected radiation so that characteristics of small portions of the structure may be detected with high precision. The method is particularly useful for scanning a regular structure such as a pipe, although the method and apparatus may be used for scanning other types of structure. In a particular embodiment of the invention, the scanning method is a method of detecting changes in the density of the wall of a pipeline. Use of this method enables flaws such as voids, cracks, scale, gas hydrates or thinning to be detected. The change in density may be detected relative to adjacent portions of the pipe wall or relative to a reference value generated from a model pipeline or a calculated value.

In the method of the invention, an array of detector units is mounted opposite at least one source of gamma radiation such that the radiation is emitted in the direction of the detecting surfaces. The target structure to be scanned is capable of being interposed between the source and detector unit so that the radiation emitted by the source can pass along a plurality of paths through a portion of the structure and impinge upon the detecting surfaces. The source and detector unit may be moved relative to the target structure (or vice versa) in order to scan different portions of the structure. The principal benefit of using an array of detectors is that different paths through the structure may be scanned simultaneously. Each of the paths has the shape of a frustum, having the source at the apex and the detecting surface of a detector at the base. Each detector in the array defines a different path through the structure so that the number of paths which may be scanned simultaneously is equal to the number of detectors in the array. The number of detectors in a detector array may vary from fewer than 10 to more than 100, e.g. up to 150, depending on the application for which the scanning method is to be used. In practice, the mass of shielding material required to shield and collimate a large number of detectors may provide a practical upper limit to the number that can be used.

The source unit and detector unit may be mounted on a support in fixed relationship to one another or the detector unit may be movable relative to the source unit. It is greatly preferred that the source unit and detector unit are mounted in a fixed relationship when the apparatus is in operation. This enables the apparatus of the invention to provide a precise and fixed alignment of source and detector units so that modulation of the counts measured by the detectors can be attributed solely to the materials between the source and detector through which the radiation path passes. In this way, very small differences in the density of such materials can be detected, allowing the detection of small flaws or changes in the thickness of a pipeline wall. The source and detector unit are preferably mounted so that the detecting surface(s) of each of the detectors form a tangent to an arc having the source at its origin. The plurality of detector units are arranged in close proximity to each other. It is preferred that the array of detector units is arranged in the form of an arc having a radius centred on the centre of the object or structure to be scanned. The design of the detector unit preferably minimises the total distance on each detection path through each detector unit in order to make the array of detector units as compact as possible, whilst maintaining sufficient depth of the collimation and a detector for efficient detection of gamma photons on each path.

In a preferred form of the invention, the source unit and detector units are mounted on a support which provides means for the structure to be scanned, or a portion thereof, to be located between the source unit and the detector unit. The support maintains the source unit and detector unit in a spaced apart fixed relationship. The support therefore includes means for mounting at least one source unit and means for mounting a plurality of detector units on the support. The support may comprise an elongate portion or "arm" having first and second opposed ends to which said detector unit and support unit may be mounted or joined. The means for mounting a detector unit comprises a detector housing joined to the support. The support, source unit, and/or detector housing may be formed as a unitary component or from separate components which are joined together. The support must be sufficiently strong to withstand supporting and moving the detector and source units without deformation and sufficiently rigid to maintain a precisely fixed relationship between the source unit and detector housing, including any detector units housed therein. One suitable material for the support comprises an aluminium alloy, which may be machined by known methods to form the required shape for the support.

The detector housing is shaped to house one or more detector units and to secure such units so that they do not move unintentionally, during operation of the apparatus. It is an important feature of the preferred apparatus that the detector units can be maintained in a fixed relationship to the source during use in a scanning method. The detector housing may be of such size and shape to house several detector units at the same time, for example from 2-100 units. The detector housing may include means to house a detector unit in more than one position within the housing. The means may simply comprise a detector housing having sufficient space to house a detector unit in more than one location within the housing. Means, such as guide rails or a motor may also be included to move one or more detector units from a first location within the housing to a second location within the housing. A practical limit on the resolution of a scanning method using an array of detectors is that the spacing between each one must be sufficient to allow a minimum required amount of shielding to ensure that each detector is adequately shielded from photons impinging on a neighbouring detector. Even when highly dense alloys are used for detector shielding, we have found that a practical limitation on detector spacing is approximately 1° of arc. In one embodiment of the apparatus, the detector housing is of such a size as to allow a detector unit to be housed in at least two positions, offset from each other by a distance which is a fraction of the distance between the detectors. When the fraction is 0.5 of the detector spacing distance (0.5 s), the resolution of the apparatus may be doubled by carrying out a first scan when the detector array is in a first position in the housing and then repeating the scan when the detector array is in a second position in the housing which is offset from the first position by 0.5 s. If additional positions are provided, and or, the angular distance between them is reduced, additional scans can provide additional data to enhance the resolution of the scan. The detector may be moved between any of the at least two positions, for example by operation of a powered switch operated by a solenoid. The provision of means to lock the detector array securely in a single position whist scanning is greatly preferred. Such means may comprise a sprung pin or boss engaging with an indexing hole in each of the desired positions.

In a particularly preferred form, the apparatus comprising support, detector housing (including any detector unit therein) and source unit may be moved laterally and/or rotationally, relative to the structure and means are provided to effect such movement. Preferably the source unit and detector units are rotated around the structure such that the radius of rotation has an origin within the structure, for example the origin may be approximately at the geometric centre of the structure in the plane of rotation. The means for said movement may include motorised or manual impulsion and guiding means such as rails, tracks, guide channels or locating indicators, to guide the path of rotation. Preferably the apparatus is provided with at least one track or rail, shaped to conform to at least a part of the structure to be scanned. For pipeline scanning, for example, one or more arcuate tracks may be provided so that the apparatus may be moved along the tracks, for example by means of a worm drive or a stepper motor turning a splined drive-wheel, gear or cog to rotate the detector housing and source around the circumference of the structure. In a preferred form, the guiding means is indexed, for example by providing indentations into which teeth of a drive cog may engage to effect movement of the scanning apparatus. The provision of indexed movement may provide a predetermined number of scanning locations at known angular positions around the structure. Preferably a means is provided to rotate the detector units and source around a circumference of the structure to be scanned. In the case of a cylindrical object, such as a pipeline, the detector units and source are rotated around the circumference of the pipeline. The scanning method is carried out at a plurality of radially offset positions around the structure so that density data may be acquired at a variety of angles through the structure.

The guiding means, e.g. tracks, may extend partially or entirely around the pipeline. It is preferred to move the source and detector unit continuously around the structure in order to avoid the problems, such as damage to the apparatus or slippage of the scanning system, associated with successively accelerating and braking the apparatus. More than one scan may be required to gather sufficient data to determine the structure properties, although the number of scans and the scanning time is dependent upon the density and mass of material through which the radiation must travel from the source to the detector units. Preferably a continuous rotational movement around the structure at a relatively low rpm, for example at from about 1 to about 20 rpm, especially from 1-10 rpm is maintained during the scanning operation. Therefore in a preferred apparatus means such as a continuous track are provided to enable such movement. The guiding means may be provide in more than one part, which, following deployment of the apparatus, are brought together and optionally joined, to form the desired length of track for scanning. The source unit, detector unit, support and guiding means may all be housed within an enclosure which is capable of surrounding at least a part of the structure. The enclosure may have an open position in which it may be positioned around the structure and a closed position in which it is capable of scanning the structure. The enclosure may take the form of a hinged pair or set of jaws which may be clamped to the structure to be scanned.

Power may be recovered from the movement of the apparatus by means of a dynamo, or similar, which may be then used to help power the detectors or other operating systems of the apparatus.

Movement of the apparatus may also involve lifting and/or sliding the apparatus manually or by mechanical means, for example by means of a remotely operated vehicle (ROV). An ROV may be preferred to deploy and move the apparatus when deployed in remote or underwater locations. Linear movement, for example parallel to the axis of a pipeline or a vessel, may be achieved by means of a crawler mechanism or using a track or rails, or alternatively by external means such as a lifting apparatus or ROV. The movement means may include indexing, for example at a particular angular separation in order to provide a predetermined number of scanning locations at known positions around the structure. For an application such as scanning a pipeline, the movement may be controlled by means of a programmed electronic control unit, for example to execute a predetermined timed movement or set of movements of the source and detector units relative to the pipeline. The movement may be rotational to scan around the circumference of the pipeline and/or lateral to move axially along the pipeline.

The apparatus may comprise means to support the apparatus in proximity to the structure to be scanned. Such means may comprise clamps, which are capable of engaging the structure and supporting the scanning apparatus in one or more positions on the structure. The clamps may be manually operated but mechanically operated clamps are preferred.

The scintillating material is selected according to the properties of the radiation which is to be detected and the conditions in which the detector is deployed. In principle, any suitable scintillating material may be selected and many materials are known and marketed for the detection of radiation. A high density material provides a greater capacity to stop radiation in a given volume and consequently the scintillator can be made smaller than would be possible for a lower density material. A small scintillator is more stable, for example it is less likely to exhibit a temperature differential between different parts of the crystal. Smaller crystals transmit light more effectively requiring lower-powered photo-detectors to be used. Of importance for the present application a small scintillator can have a small detecting surface and so radiation travelling along a narrow path can be detected without a significant amount of incident radiation from background or scattered radiation from the same or different paths. For the detection of gamma radiation, it is preferred to use a dense inorganic material so that the incident photons may be stopped using as small a detector as possible. Scintillating materials having a density>5 and a high Z-number (atomic number) are preferred. It is preferred that the scintillator(s) have a depth and density that enable them to stop >80% of gamma photons of energy of 662 keV. For use in applications requiring resistance to environmental conditions, especially moisture, a non-hygroscopic crystal scintillator should be selected. Especially preferred detectors for use with gamma radiation include BGO (bismuth germanate), $CdWO_4$, $LaBr_3(Ce)$, LYSO (lutetium yttrium oxyorthosilicate—cerium doped), LSO (lutetium oxyorthosilicate—cerium doped) and $CeF_3$ (cerium fluoride). When a mechanically rugged detector is required, a crystal having no cleavage planes may be preferred in order to increase its resistance to shattering following a thermal or mechanical shock.

Each scintillator has a detecting surface, which, in use is arranged to intersect the radiation path so that the radiation impinges upon the detecting surface. Other surfaces of the detector which are not arranged to be detecting surfaces will be referred to as non-detecting surfaces. Although any part of a scintillator is normally capable of detecting photons, the designation in this specification of detecting surfaces and non-detecting surfaces refers to the arrangement of the scintillator in the detector unit for detecting radiation from a source. The scintillator also has a surface through which light generated by the scintillator in response to photons impinging upon the detecting surface leaves the scintillator. This surface is referred to herein as the collecting surface. The collecting surface is arranged in optical communication with the photodetector. The collecting surface can be in contact with the photodetector or it may be separated therefrom by one or more light transmitters, in the form of a window, lens, optical fibre, light pipe or optically coupling material etc. made from a material which transmits the light generated by the scintillator to the photodetector. The collecting surface of the detector may have a similar cross-sectional area and shape to that of the photodetector window or it may be different. The detector itself may act as a light guide to pass a substantial proportion of the light generated in the scintillator to the photodetector. In this context, the use of the phrase "substantial proportion" means all of the light generated in the scintillator is passed to the photodetector, save for a proportion of light that is unintentionally lost due to the efficiency of the light transmission being less than 100%.

Each of the detectors comprises a scintillator, normally supported in a suitable position so that the detecting surface intersects a path of radiation emitted by the source at a particular distance from and a particular angle to the radiation source. It is a particular feature of the invention that the detector can substantially reduce the detection of scattered radiation and increase the precision with which radiation emitted by a source along a particular linear path is detected. The provision of a detector having an elongate shape in which t≤h, more preferably <0.5 h, at the detecting surface enables the detectors to be located in close proximity so that spatial resolution of each detector is high. The depth of the detector contributes to the stopping efficiency of the detector so that a detector having a depth d perpendicular to the detecting surface at least 2t, more preferably at least 5t, especially >10t is preferred in order to stop and measure energetic photons.

The smallest dimension of the detecting surface of the scintillator is preferably between about 1 mm and about 10 mm. The smallest dimension is defined to be the thickness t of the material. More preferably, 1 mm≤t≤5 mm and in a preferred embodiment t is about 5 mm. Preferably the detecting surface is generally rectangular so that the area of the surface is defined as t×h, where h is in the range 5-100 mm. More preferably, 10 mm≤h≤50 mm and in a preferred embodiment h is about 25-40 mm. The depth, d of the scintillator is in the range 10-100 mm. More preferably, 25 mm≤d≤75 mm and in a preferred embodiment d is about 40-60 mm.

A material which is impermeable to the radiation may cover a part of the detecting surface of the scintillator to delimit the portion of the detecting surface on which radiation may impinge. The collimator may overlap and cover one or more edges of crystal by up to about 5 mm.

The detection of scattered photons is preferably further reduced by preventing the detectable radiation from impinging upon the surfaces of the detector which are not detecting surfaces. This may typically be achieved by covering the non-detecting surfaces, except for the portion of the collecting surface in optical communication with the photodetector, with a material which prevents transmission of the radiation to the non-detecting surfaces. In a preferred embodiment the detectors are surrounded by shielding material so that all of the non-detecting surfaces, except for the portion of the collecting surface in optical communication with the photodetector, are protected from radiation. By shielding material we mean a material which is highly attenuating to the radiation which is to be detected by the detector. Typically, a shielding material for protection from ionising radiation such as gamma radiation includes lead and heavy metal alloys. Such materials are well known to persons skilled in the art of designing radiation detectors and nucleonic instruments.

When the scintillator is thin, scintillation light generated as a result of the interaction of a gamma photon with the scintillation material is likely to be internally reflected several times before it enters the photodetector. Since each reflection may be less than 100% efficient, the capacity for multiple reflections provides multiple opportunities for loss of light and thus a decrease in the detection efficiency of the detector. It is therefore preferred to provide the non-detecting surfaces with means to reflect light internally within the detector. Preferably the non-detecting surfaces are coated with a super-reflective coating, capable of reflecting at least 95% of the light within the scintillator and more preferably at least 98% of that light.

When the detector unit comprises more than one detector, deployed in the form of an array of detectors, a preferred embodiment of the invention comprises a block of shielding material (a "detector block") having openings extending inwardly from a surface of the block, each opening containing a detector, the detecting surface being accessible to radiation from outside the block. A portion of the detecting surface may be covered by shielding material for the purposes of delimiting the area of the detecting surface or for mechanically retaining the detector within the opening. The non-detecting surfaces of the detector may optionally be enclosed partially or wholly within the opening and covered by the shielding material. The detector block includes means by which the collecting surface of the scintillator(s) may be brought into contact with a photodetector or a light transmitter. Such means may take the form of an open passage through which the scintillator extends so that the collecting surface is accessible to the photodetector or light transmitter.

The precision of the detector is increased by providing collimation means for restricting the path along which radiation may travel to the detecting surface. The collimation means comprises a collimator formed from a shielding material and arranged so that radiation travelling towards the detecting surface from selected directions may contact the detecting surface whilst radiation travelling from non-selected directions is excluded from the detecting surface. In this way, only radiation travelling along selected paths from a radiation source to the detector may be detected. The collimation may be arranged so that radiation from one or more selected radiation sources is detected. Suitable design of the collimation can significantly reduce the detection of scattered photons, which are usually deflected from the path along which they were emitted by the source. Alternatively, the collimation may be designed so that scattered photons and other secondary radiation is detected preferentially. In a preferred embodiment the collimation means comprises a block of shielding material having a channel, or preferably a plurality of channels extending through. The collimator block comprises a plurality of channels, each channel being formed through the block and corresponding in position to one of the detectors in said array. Each channel is shaped to define the path of radiation which is to be detected by each scintillator. Each channel has an opening at the end proximal to the scintillator which is preferably mounted over the detecting surface of the scintillator so that the detecting surface, or a portion of it, is within the opening of the channel. The end of a channel distal to the scintillator is open to allow radiation to enter the channel and travel to the scintillator. The opening preferably lies on the plane of a tangent to a circle having the source as its origin. The area of the distal opening defines the maximum useful area through which radiation can pass to the detecting surface. The channel walls are normally straight. The length of the channel(s) is determined according to the requirements of the detector and the energy of radiation emitted by the source. A longer channel reduces the detection of scattered or reflected radiation more than a shorter channel and so the resolution of detection of a particular path of radiation is higher. The length of the collimation channels may be determined by the skilled person according to the type of radiation which is to be collimated, in accordance with known principles of physics. Generally for collimating radiation from a caesium source (which is a preferred source for use in the method and apparatus of the invention), a collimation depth of at least 50 mm should be used. A cobalt source requires more collimation and generally a depth of at least 75-80 mm would be used. Americium emits less energetic gamma radiation and requires only about 20 mm of collimation depth. Americium may be used in some applications but would not be suitable for use in scanning steel pipelines, which is a preferred application. The depth, d of the collimator channels is preferably in the range from 30-150 mm. More preferably $50 \leq d \leq 150$ and, for use with a caesium source suitable for scanning large pipelines d is most preferably about 80-120 mm.

The cross-section of the channel may be any convenient shape, although it is preferred that the channel has the same shape and orientation as the detecting surface. Often, the channel has a generally rectangular cross section. The shape and/or size of the channel cross-section may change along the length of the channel, or they may remain substantially constant. In a preferred embodiment, at least one of the collimator channels has at least one wall defining the channel which is aligned with a radius of a circle having the source as its origin. Preferably each of the walls of the channel is aligned with a different radius of said circle so that the opening of the channel is aligned to face directly towards the source. Preferably, in such an arrangement the end of the collimator distal to the scintillator has an opening lying on the plane of a tangent to a circle having the source as its origin. In this way the detection of photons travelling in a straight line from the source, through the target structure along the collimator channel to the detector may be maximised for any given area of detecting surface. More preferably all of the collimator channels have at least one wall and preferably all of their walls, aligned with the radius of a circle having the source as its origin. In such an arrangement the walls of the collimator channels are not parallel to each other and all of the channels face the direction of the source. When this alignment of the collimator channels is adopted, and the array of detector units is arranged in an arc having an origin which is not the source, at least some the collimator channels do not extend in a direction which is perpendicular to a tangent to that arc. This is a preferred arrangement for scanning a cylindrical structure such as a pipeline. In order to produce the collimator channels having this preferred alignment, it is preferred to form each channel in a block of shielding material by means of a machining method. For this reason the use of plates of shielding material, e.g. steel plates, of the type found in the detector units of x-ray tomography apparatus (for example as described in U.S. Pat. No. 4,338,521) is not preferred.

In one embodiment of the apparatus of the invention, the detector unit comprises a collimator block and a detector block, joined together such that the proximal end of each channel is in register with the detecting surface of a detector. The detector block and collimator block are joined together so that the connection between them does not allow radiation to impinge on the detecting surface of a detector which has not traveled through a channel in register with the detecting surface. It may be possible to form the detector block and the collimator bloc from a single piece of shielding material but it is normally easier to manufacture them separately and then join them together.

The collimator block may be formed from a dense shielding material such as lead or a heavy alloy which attenuates gamma radiation. Alternatively, the collimator block may be formed, at least in part, from a less dense material, such as steel for example, which provides less shielding but which is not as heavy as the more dense shielding materials such as lead or heavy alloy. In one version of such a collimator, collimator channels are formed from a first material, such as steel, and a layer of a second material, such as a heavy alloy, having a greater shielding capacity than the first material, is positioned over at least one external surface of the detector unit. In this way the detector unit may be better protected from the impact of scattered radiation from selected directions than from other directions. In practice, it is possible to determine, by calculation and/or modelling, the probability at which gamma radiation scattered from particular angles will impinge upon the detector unit. This information may then be used to provide more shielding over those surfaces of the detector unit at which scattered gamma photons are more likely to contact the detector units. More shielding can be provided either by using a more dense material or by increasing the thickness of the shielding material. One advantage of providing different shielding at different parts of the detector unit, or forming the detector unit from different materials is that the weight of the detector unit can be reduced whilst the shielding and collimation of the detectors is substantially maintained. A further advantage of using a material such as a steel to form at least a part of the collimator is gained if the material has greater structural strength than a traditional dense shielding material such as lead or heavy alloy so that less structural support must be used to support the collimator block.

The photodetector may be a photodiode, photomultiplier tube (PMT) or other suitable light detecting device. Currently, PMTs are preferred to photodiodes because they are more sensitive to very low levels of light, although the use of other photodetectors, such as silicon photomultipliers or avalanche photodiodes may become preferable as technology develops. The photodetector generates an electrical signal in response to light entering it through an optical window. The wavelengths detected by the photodetector should be matched as far as possible to the wavelengths generated by the scintillator to maximise the detection efficiency. Normally a photodetector is provided for each scintillator so that the amount of radiation detected by each scintillator can be measured independently of the other scintillators.

The photodetectors are held in position by attachment means such as a clamp or mounting. When more than one photodetector is present, they may be mounted in fixed positions within a mounting block. The mounting block is formed from a material which is impermeable to light and to any other radiation which is likely to affect the signal produced by the photodetector. The photodetector is mounted with its optical window optically coupled to a collecting surface of the scintillator. The photodetector may be coupled using an optically coupling adhesive. Selection of a suitable optical coupling material such as an adhesive having some resilient elastic properties can provide the detector unit with some resistance to the effects of vibration or impact shock. Normally the photodetector is adjacent the scintillator, but it may be physically separated from the scintillator if light transmitting means are provided to transmit light from the scintillator to the photodetector. In that case it is important that the efficiency of the light transmission is as high as possible.

The photodetector may be in a coaxial relationship with its respective scintillator and collimator. Alternatively, the photodetector may be mounted at an angle to the axis of the collimator and scintillator, for example at an angle of between about 45 and 100 degrees to that axis, especially about 90°. One advantage of mounting the photodetector at an angle to the axis of the scintillator and collimator is that the total depth of the detector unit may be reduced compared with a detector unit in which the photodetector is mounted coaxially. Reducing the depth of the detector unit helps to minimise the space needed around the target structure to carry out a scan and this can allow scanning in restricted spaces and/or minimise the need for trenching a pipeline prior to scanning.

In a preferred embodiment of the invention an array of n detector units is provided, comprising an array of n radiation detector comprising:
n scintillators,
n photodetectors, each photodetector being optically coupled with a respective scintillator,
a detector block made of highly attenuating material incorporating a plurality of n channels extending through the detector block from a first surface to a second surface, each channel being sized to accommodate a single scintillator, and
a collimator block comprising a block of shielding material having n channels extending therethrough, and wherein the collimator block is joined to the detector block so that each channel is in register with a scintillator.
wherein each scintillator is located within a channel in the detector block,
where n=an integer in the range from 2-150.

Each detecting surface preferably forms a tangent to an arc of a circle having a radiation source as its origin. In one embodiment, each detector surface forms a tangent to the surface of a part of a sphere having the radiation source as its origin.

The source unit comprises a source of penetrating radiation, a source-holder and a collimator. The collimator and source-holder may be combined. The collimator is formed of a material which is highly attenuating to the radiation emitted by the source and is normally formed of a heavy alloy material of the type known and commonly used for shielding radiation of the appropriate energy and type. The collimator is located and adapted to limit the radiation emitted by the source unit to a predetermined beam shape and direction. Preferably the radiation beam is shaped by the collimator to form a fan, cone or frusto-cone, or sector in each case having the source as origin. A preferred beam shape is a cylindrical sector, i.e. a sector having a thickness rather than being planar. Preferably the beam is collimated to provide a beam area at the location of the detector(s) which has the same general shape and area as the combined detecting surface(s) of the array of detectors. In the preferred form of the apparatus, the source unit is mounted on a support, preferably in the region of an end of an elongate support.

The radiation source is selected by the transparency to the radiation of the material(s) to be measured, e.g. a vessel and/or its contents (i.e. the attenuation coefficient of the medium) and the availability of suitable sources and detectors. For scanning large solid structures such as process vessels and pipelines, suitable sources of gamma include $^{60}$Co and $^{137}$Cs, $^{133}$Ba, $^{241}$Am, $^{24}$Na and $^{182}$Ta, however any gamma-emitting isotope of sufficient penetrating power could be used, and many such are already routinely used in density gauges, such as those used as level measurement devices. Usually, the half-life of the radioisotope used will be at least 2, and desirably at least 10, years. The half-lives of the radioisotopes mentioned above are: $^{137}$Cs gamma about 30 years, $^{133}$Ba about 10 years and $^{241}$Am about 430 years. Suitable sources generally emit radiation at energies between about 40 and 1500 keV.

The source unit may include one or more than one source. The scanning method may utilise more than one source unit if required.

The apparatus further comprises a signal/data processor for operating on the electrical signal from the detectors in the detector unit(s) and a controller to control the operation of the apparatus. Signals representative of the counts of photons detected by the scintillators are processed by the data processor. The signal may be subjected to smoothing or stabilisation algorithms, averaged or otherwise operated on according to standard practices. A data processor may perform calculations based on the signal from the radiation detector or from a signal processor if present. The data processor may output information concerning the amount of radiation measured over a time interval, or it may further calculate derived properties of the scanned structure, usually in the form of a bulk density or a change in bulk density between radiation paths through the structure. The scanning method is carried out at a plurality of radially offset positions around the structure so that density data may be acquired at a variety of angles through the structure and a tomography algorithm may be used to provide information about the changes in density at different paths through the structure. In a preferred form the data from the detectors is operated on by the data processing unit using tomography algorithms in order to produce a graphical representation of the density or composition of the structure along different paths. The data processor may contain a calibration or information concerning the radiation source. The data processor output is may be connected a display or a (optionally wireless) transmission means so that a signal can be sent from the apparatus to a remote location. Alternatively a signal comprising data from the radiation detector itself may be sent, for processing at a remote location. A power supply is provided to power the photodetectors, data processor and control electronics and also to power motors for moving the apparatus.

In use in the scanning method of the invention, the apparatus is deployed so that the source unit and detector units are positioned in relation to the structure to be scanned so that one or more radiation paths from the source to detectors in the detector unit pass through the desired portion of the structure. The amount of radiation, in the form of counts, is measured by the detector in each detector unit deployed in the apparatus. The scanning method is carried out at a plurality of radially offset positions around the structure so that density data may be acquired at a variety of angles through the structure. The apparatus may then be moved to a different location or orientation with respect to the structure and the measurement is repeated. In this way a record of the attenuation to radiation through each radiation path through the structure may be gathered and used to calculate the location of changes or to build a representation of the structure and its contents. Information such as changes in density which may highlight flaws or other features within the structure can be obtained from the data gathered from the detectors using data analysis tools known for use in tomography methods.

For operation underwater, it is preferred to increase the buoyancy of the apparatus by means of a buoyancy block. If used, the buoyancy block may be attached to the apparatus by means of a flexible attachment so that the flotation force produced can be balanced during movement of the apparatus. Additionally or as an alternative, spaces within the apparatus may contain a foam material in order to provide positive buoyancy to the apparatus. Parts of the apparatus may be coated in a resilient foam material, again for the purpose of providing buoyancy and also to protect the apparatus from physical damage, such as impact damage, and environmentally induced damage such as corrosion.

BRIEF DESCRIPTION OF THE DRAWINGS

The invention will be further described with reference to the attached drawings, which are:

FIG. 1: a schematic view of a scintillator suitable for use in the scanning method and apparatus of the invention FIG. 1A: A view of the scintillator of FIG. 1 from direction A.

FIG. 1B: A schematic view of an alternative scintillator suitable for use in the scanning method and apparatus of the invention.

FIG. 2: a schematic view through a section of a detector unit.

DETAILED DESCRIPTION OF THE PREFERRED EMBODIMENTS

Figure 4:
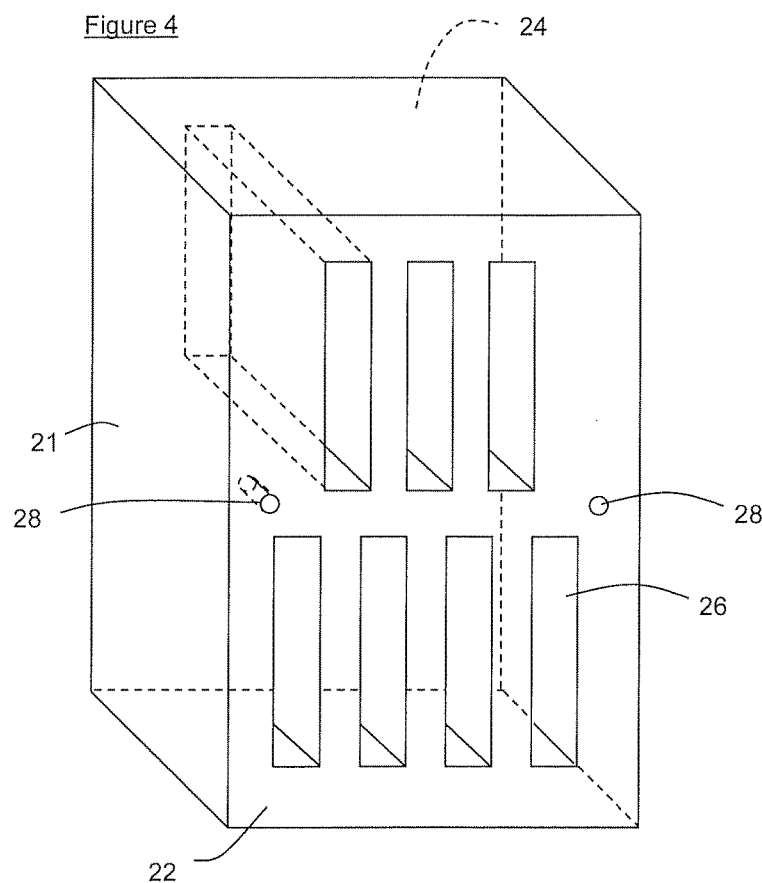
FIG. 4: a schematic view of a detector block forming part of a radiation detector according to the invention.

FIGS. 1 and 1A show a bismuth germinate (BGO) scintillator crystal 10 having a thickness t of 5 mm, a height h of 30 mm and a depth d of 75 mm. The detecting surface 12 is opposite the collecting surface 14. All surfaces of the bismuth germanate (BGO) scintillator crystal 10 except the detecting surface 12 and collecting surface 14 are coated in a highly reflective coating. FIG. 1B shows an alternative bismuth germanate (BGO) scintillator crystal 10.

FIG. 2 shows, a transverse cross-section through a detector unit 30, comprising a block of heavy alloy 16 which is highly attenuating to radiation, of the type used as shielding material for gamma radiation. The block of heavy alloy 16 has collimation channels 18 extending from the front face to the opposed rear face of the block of heavy alloy 16. In use, a bismuth germanate (BGO) scintillator crystal 10 is housed in the block of heavy alloy 16, with the detecting surface 12 of the bismuth germanate (BGO) scintillator crystal 10 at the front face of the block of heavy alloy 16 and the collecting surface 24 optically connected to photomultiplier tube (PMT) 20. Photomultiplier tube (PMT) 20A is connected to an adjacent bismuth germanate (BGO) scintillator crystal 10 (not shown), and is shown to demonstrate the packing of the photomultiplier tubes (PMTs) within the detector unit 30. The detector unit 30 comprises nineteen detectors, each comprising a bismuth germanate (BGO) scintillator crystal 10 and a photomultiplier tube (PMT) 20 and mounted in register with a collimation channel 18 in the block of heavy alloy 16.

Figure 5:
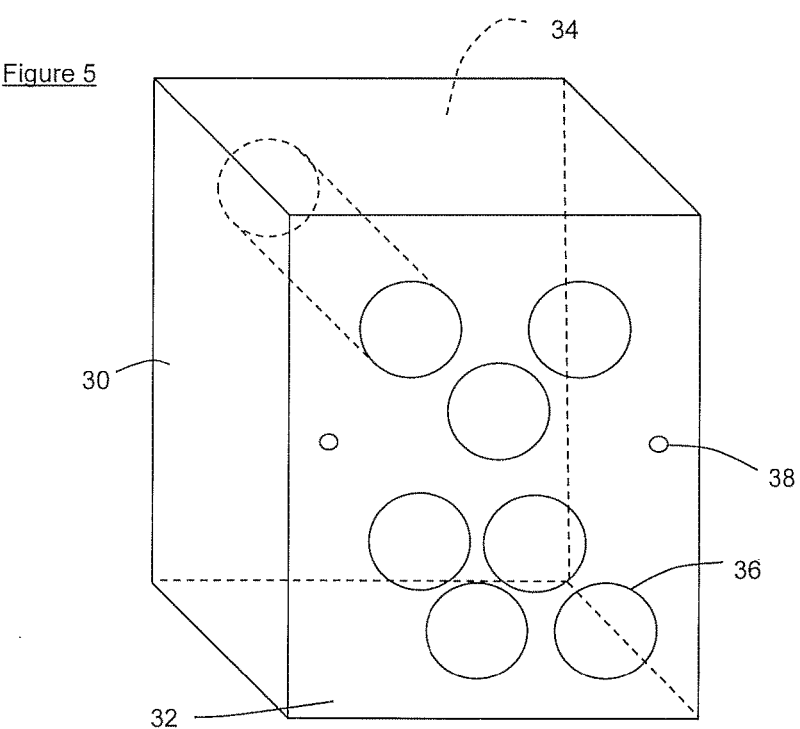
FIG. 5: a schematic view of a photomultiplier mounting block forming part of a radiation detector according to the invention.
Figure 6:
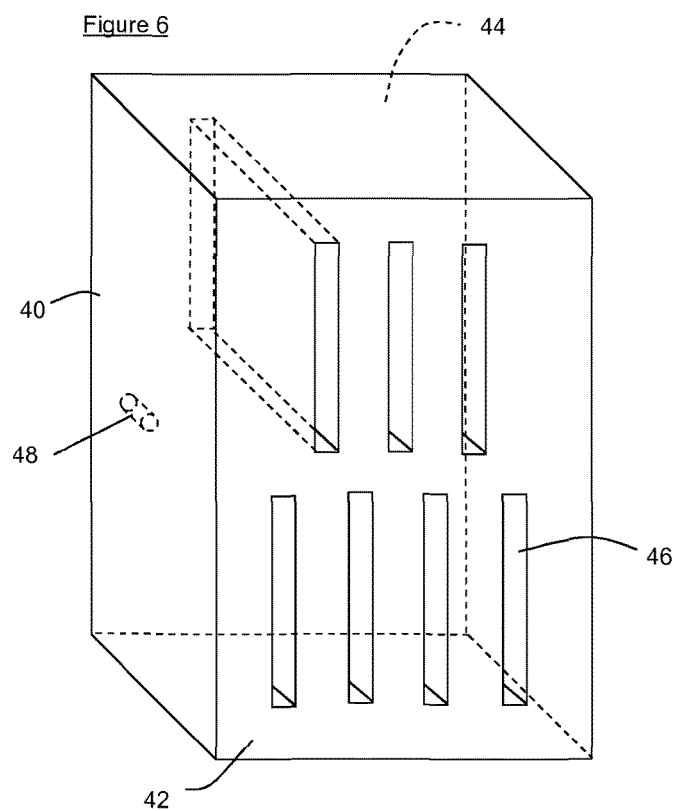
FIG. 6: a schematic view of a collimator block forming part of a radiation detector according to the invention.
Figure 3:
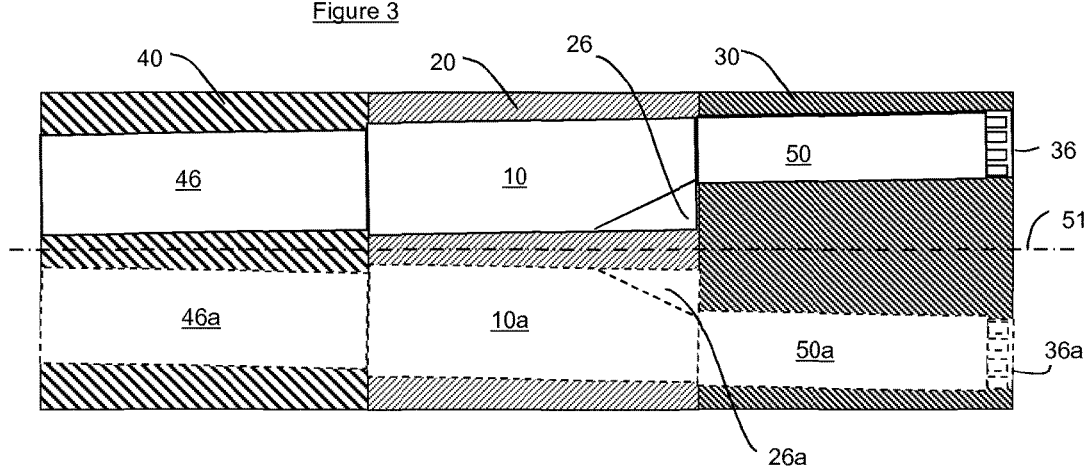
FIG. 3: a schematic view through a longitudinal section of a detector unit

FIG. 3 shows a longitudinal section through an assembled radiation detector comprising a collimator block 40, a detector block 200 and a PMT mounting block 300, each shown individually in FIGS. 4-6. The blocks are mounted together so that channels 46, 36 and 26 are all in register, together forming channels extending from the front face of the collimator block 40 to the rear of the PMT mounting block 300. A scintillator crystal 10 is housed within channel 26 and a PMT 50 is housed within channel 36. The PMT 50 may be connected to electronic data processing and control apparatus by means of connectors accessible from the rear of the channel 36. Channels 46a, 36a and 26a and the scintillator 10a and PMT 50a are shown in dashed outline because they are not in the same plane as the respective channels and components in solid outline. In the embodiment shown, the longitudinal axes of the channels 26, 36, and 46 form an angle of between 1 and 2° with the longitudinal axis 51 of each block 200, 300, and 400.

FIG. 4 shows a detector block 200 which comprises a rectangular block of heavy alloy 21 which is highly attenuating to radiation, of the type used to as shielding material for gamma radiation. The rectangular block of heavy alloy 21 has channels 26 extending from the front face 22 of the rectangular block of heavy alloy 21 to the opposed rear face 24. Blind sockets 28 are provided for locating and mounting a collimator block. The channels 26 are sized to house a scintillator crystal. In use, a scintillator crystal is housed in each channel 26, with the detecting surface of the scintillator crystal at the front face 22 of the rectangular block of heavy alloy 21 and the collecting surface at the rear face 24.

FIG. 5 shows a photomultiplier mounting block 300 which comprises a rectangular block of white plastic material such as polytetrafluoroethane. Channels 36 extend from the front face 32 of the photomultiplier mounting block 300 to the opposed rear face 34. The channels 36 are each of an appropriate size to house a small photomultiplier tube. The channels 36 are positioned in the photomultiplier mounting block 300 in such a way that each opening at the front face 32 of the photomultiplier mounting block 300 butts against the collecting surface 14 of a scintillator crystal 10 mounted in an adjacent detector block 200 when the rear face 24 of the detector block 200 is placed against the front face 32 of the PMT mounting block 300. Blind sockets 38 are provided for locating and mounting to the detector block 200.

FIG. 6 shows a collimator block 40 comprising a rectangular block of heavy alloy which is highly attenuating to radiation, of the type used to as shielding material for gamma radiation. The collimator block 40 has channels 46 extending from the front face 42 of the collimator block 40 to the opposed rear face 44. Blind sockets 48 are provided for locating and mounting a detector block 200. The block channels 46 have a width and height which is slightly less than the width and height of the channels 26 in the detector block 200. In an assembled radiation detector, rear face 44 of collimator block 40 is mounted against the front face 22 of detector block 200 such that channels 46 are in register with channels 26.

Figure 10:
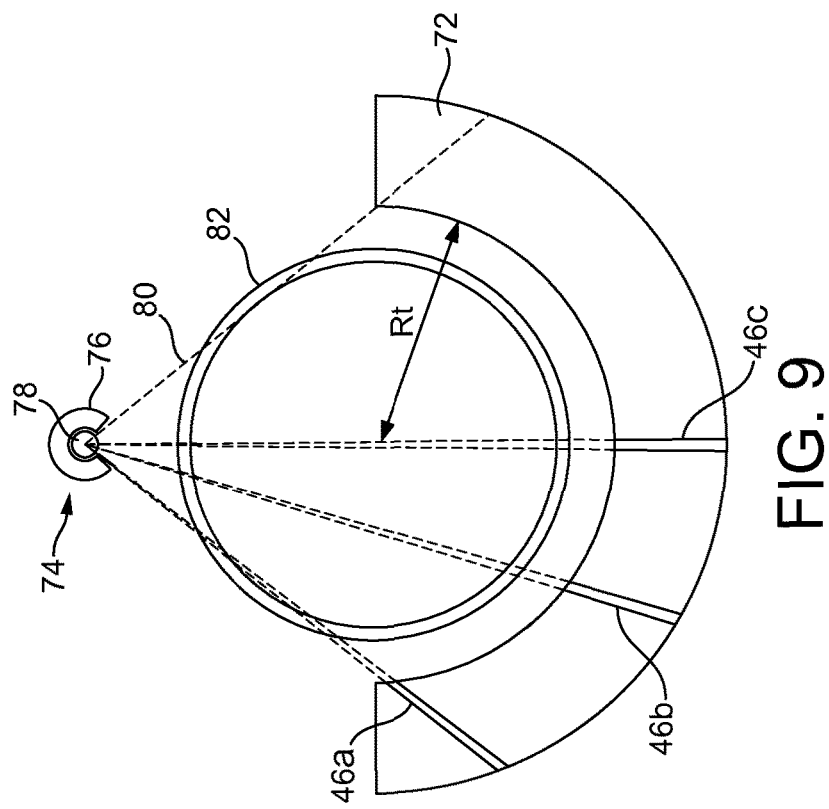
FIG. 10: a schematic view of an array of detector units for an apparatus according to the invention

In FIG. 10, a detector unit 30 consisting of 19 collimation channels 18, scintillator crystals 10 and photomultiplier tubes (PMTs) 20 is shown, in which the collimation channels 18 are formed into a single block being spaced apart and angled from each other by an angle of about 1 degree of arc.

Figure 7:
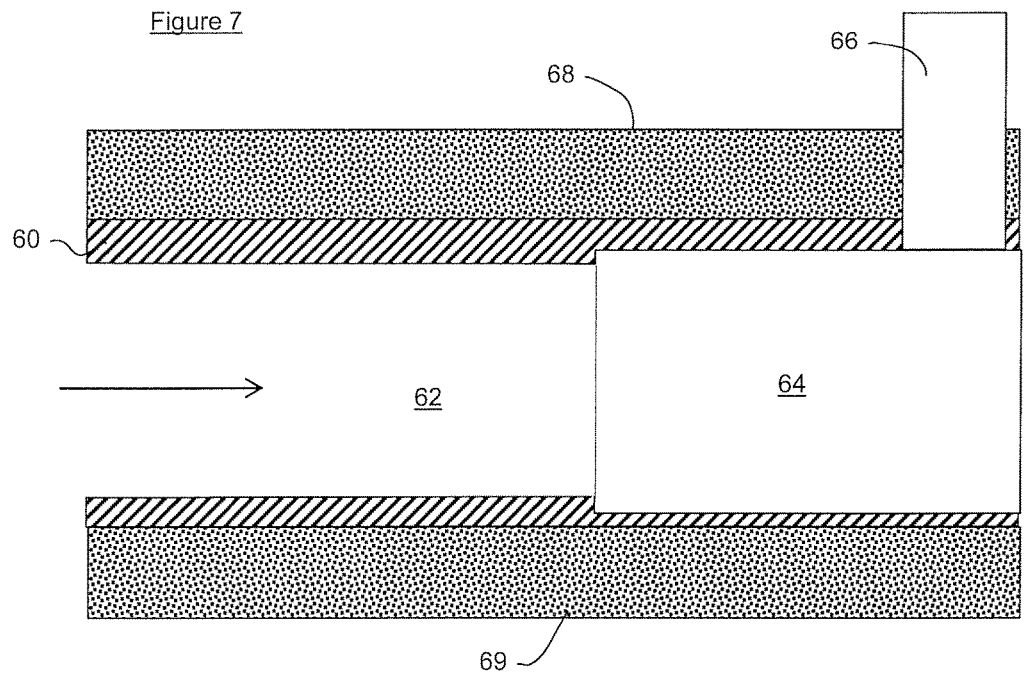
FIG. 7: a schematic view through a section of an alternative detector unit
Figure 8:
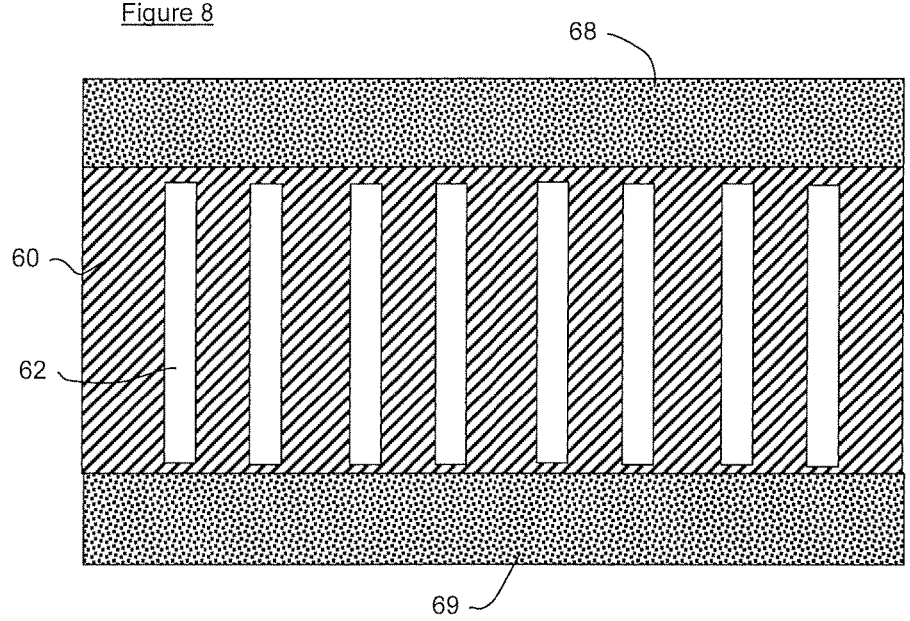
FIG. 8: a view of a front elevation of the detector unit of FIG. 7.

FIGS. 7 and 8 show an alternative arrangement for a detector unit. In FIG. 7, the steel block 60 forming the collimator 62 and holding the scintillator 64 and PMT 66 is formed from a stainless steel. The PMT 66 is mounted out of alignment with the radiation direction in order to reduce the total depth of the detector unit. The direction of radiation is indicated by the arrow. FIG. 8 shows an elevation from the direction of the arrow. Layers 68 and 69 of a dense heavy alloy shielding material are positioned above and below the steel block 60. This material provides additional shielding for the detectors from scattered radiation impinging on the detector unit.

Figure 9:
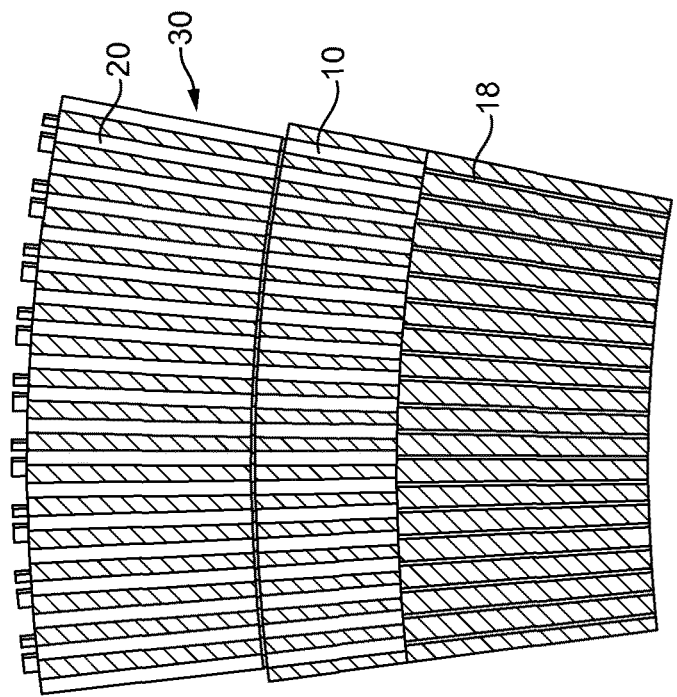
FIG. 9: a diagrammatic view of a preferred arrangement of the apparatus.
Figure 11:
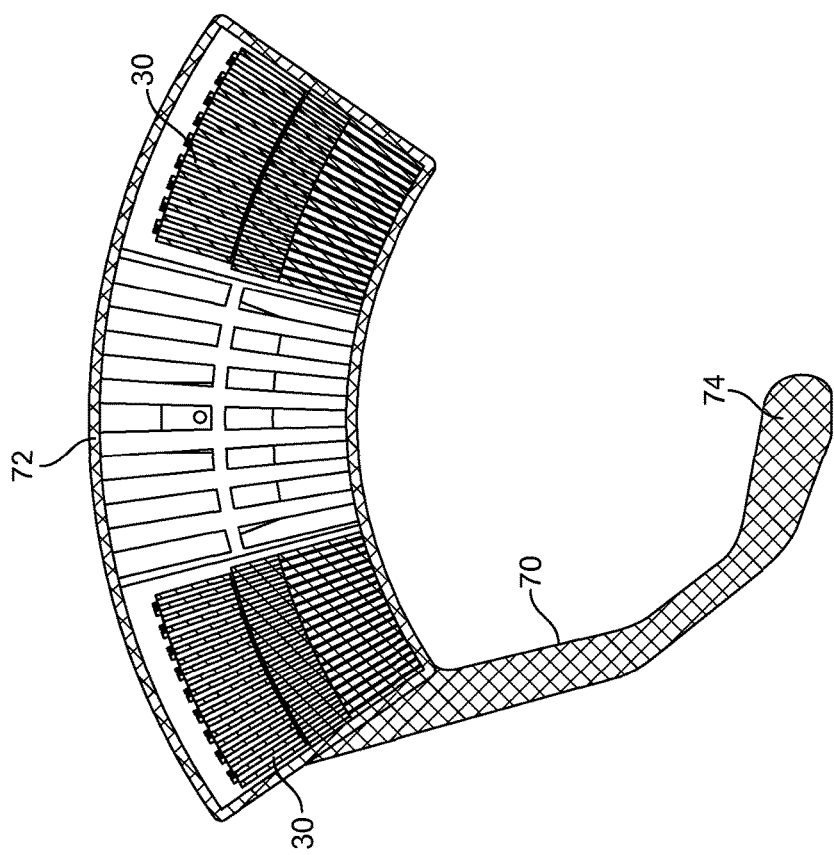
FIG. 11: a schematic view of a part of an apparatus according to the invention.

FIG. 11 shows a support 70 joined rigidly at one end to a generally arcuate shaped detector housing 72, all formed of an aluminium alloy, and at the other end to a source unit 74. An arrangement of the source unit 74 and detector units is shown in FIG. 9. The direction of three collimator channels is illustrated in order to show that they align with the direction of the source unit 74 and are not aligned with the radius Rt of the structure. The source unit 74 and detector housing 72 is arranged to rotate about a central point on the structure on a path having a radius Rt. The source unit 74 comprises a caesium source 78 of gamma radiation surrounded by heavy alloy shielding material 76 including a slot for collimating radiation in a fan shaped beam 80 towards the detector housing 72. The detector housing 72 comprises an aluminium alloy cage and, in the embodiment shown, contains two arcuate arrays of detector units 30, one at each end. The detector housing 72 includes rails along which the detector units may be moved to different locations within the detector housing 72. The detector housing 72 shown could accommodate one or more additional detector unit arrays if required.

Figure 12:
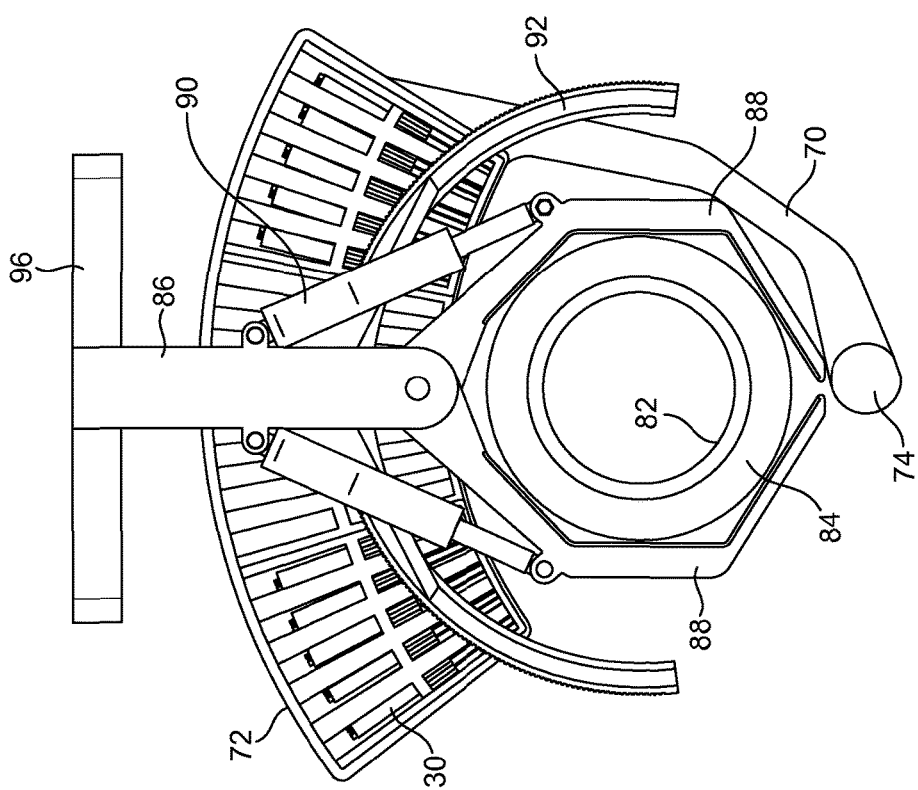
FIG. 12: a schematic elevation view of an apparatus according to the invention
Figure 13:
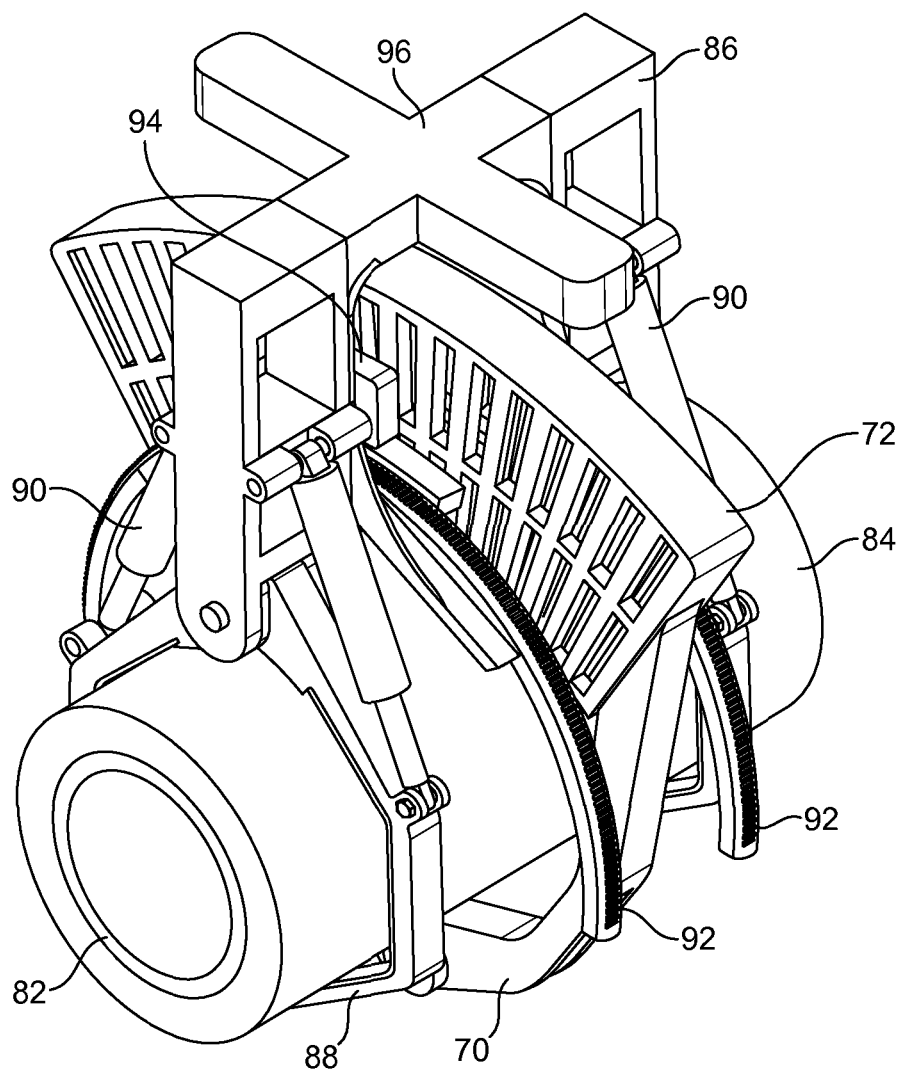
FIG. 13: a schematic perspective view of the apparatus shown in FIG. 12.

FIGS. 12 and 13 show an apparatus for scanning steel pipe 82, having an internal diameter of about 234 mm and a wall thickness of about 43 mm, to detect changes and flaws in the wall. The pipe wall is surrounded by a layer of insulating material 84. A support member 86 is clamped to the pipeline by means of clamps 88 hydraulically operated by arms 90. The support member 86 also supports rails 92 which support the support 70, detector housing 72 and source unit 74. A motor 94 mounted on the detector housing 72 is operable to move the detector housing 72 and source unit 74 along the rails 92 and thereby to rotate the position of the source and detectors around the pipeline. At each position, radiation emitted by the source towards each detector in the two detector units forms a number of radiation paths through the pipe wall and insulation equal to the number of detectors, which in this case is (19×2)=38 separate paths which can be scanned at the same time. When the apparatus is rotated to a different position along the rails 92, a further 38 paths can be scanned. Data in the form of counts detected by the detectors is processed and stored by a data processor housed in housing 96 located towards the top of the support 70. Deployment of the detector units in the positions shown is particularly suitable for scanning the pipeline walls and insulation to detect flaws and changes between different locations in the pipe.

In the detector housing 72 shown, there is space for one or more detector units to be placed in the central portion of the housing 96. In that position, a detector unit would detect radiation which has passed through the lumen of the pipe 82 and its contents. Use of a detector unit in such a position would therefore be suitable for conducting tomography scans of the pipe 82 and contents.

Figure 14:
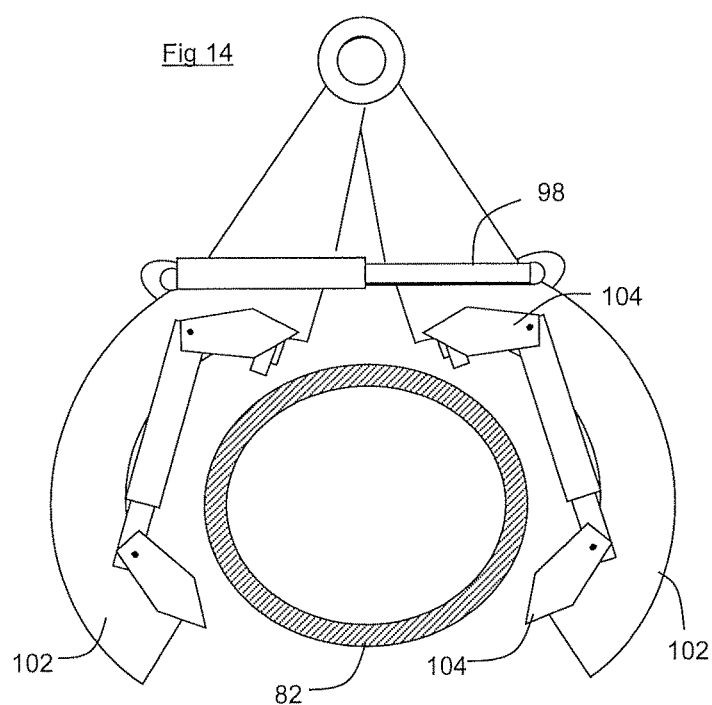
FIG. 14: a schematic elevation view of an apparatus according to the invention.
Figure 15:
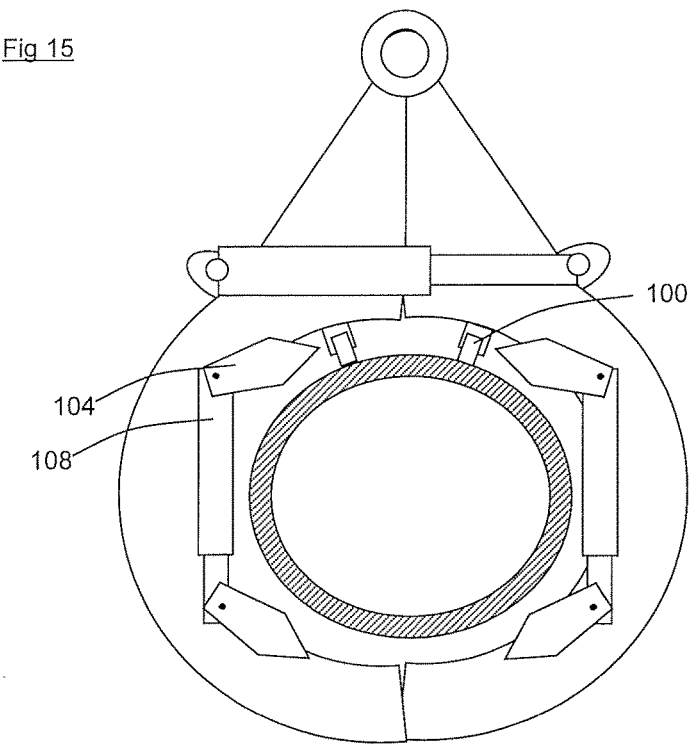
FIG. 15: a schematic elevation view of an apparatus according to the invention.

FIGS. 14-15 show another embodiment of a scanning apparatus according to the invention. The apparatus comprises two parts of a hinged housing 102 which together form a clamp with jaws which can be opened (FIG. 14) and closed (FIG. 15) around the pipe 82 by operation of a hydraulic cylinder 98. When closed, the hinged housings 102 surround the pipe 82 but are spaced apart from the surface of the pipe 82. Rollers 100 contact the surface of the pipe 82 and maintain the spacing of the hinged housing 102 from the pipe 82. Hinged housing 102 covers and contains a detector housing for one or more arrays of detector units and a source unit 74 as described above. The source and detector unit are mounted in a fixed relationship to one another and are arranged to move along a track within the jaws so as to rotate around the circumference of the pipeline. Adjustable grippers 104 are present either side of the pipe 82 which are operable by means of a hydraulic cylinder 108 to grip the pipe 82 and centralise it within the space between the jaws and the pipe 82. When the hinged housing 102 is closed around the pipe 82 and centralised by the adjustable grippers 104, the source unit 74 and detector housing 72 are rotated around the pipe 82 so that density information can be acquired by the detectors at a plurality of angular locations around the pipe 82. The data is then processed to produce a tomography image or an indication of one or more properties of the pipeline at different locations around the path of the scanning operation. When sufficient data has been acquired, the hinged housing 102 is opened and moved to a different location along the pipeline for new scanning data to be acquired.

The invention claimed is:

1. A method of scanning a sub-sea pipeline to detect changes in density between different parts of the sub-sea pipeline, the method comprising:
    providing at least one source of gamma radiation and a plurality of detector units configured to detect gamma radiation, each detector unit of the plurality of detector units comprising:
        i. a radiation detector comprising a scintillator comprising a scintillating material and having a detecting surface defined by its thickness t and height h, wherein t≤h at the detecting surface and having a depth d perpendicular to the detecting surface at least 2t,
        ii. a photodetector configured to detect light emitted by the scintillator in response to gamma radiation, and
        iii. a collimator disposed between the scintillator and the at least one source of gamma radiation;
    rotating the at least one source of gamma radiation and the plurality of detector units in a radius of rotation around an origin in the sub-sea pipeline;
    providing a guiding system to guide said rotating in the radius of rotation around the origin in the sub-sea pipeline, the guiding system being indexed;
    causing said at least one source of gamma radiation to emit gamma radiation along a plurality of predetermined radiation paths towards said plurality of detector units, the plurality of predetermined radiation paths passing through at least a portion of said sub-sea pipeline;
    measuring a number of photons of gamma radiation detected by each one of said plurality of detector units; and
    calculating a density value for each path from the number of photons of gamma radiation detected by each detector unit associated with the respective path.

2. The method according to claim 1, wherein providing the at least one source of gamma radiation and the plurality of detector units comprises arranging the plurality of detector units in close proximity to each other in the form of an arc having a radius centered on the center of the sub-sea pipeline to be scanned.

3. The method according to claim 1, wherein providing the at least one source of gamma radiation and the plurality of detector units comprises mounting the at least one source of gamma radiation and the plurality of detector units spaced apart on a support which provides a scanning device such that at least a portion of the sub-sea pipeline to be scanned is located between the at least one source of gamma radiation and the plurality of detector units.

4. The method according to claim 1, wherein 1 mm≤t≤5 mm, 10 mm≤h≤50 mm, and 25 mm≤d≤75 mm.

5. The method according to claim 1, wherein a depth of the collimator of each detector unit is in the range 50-150 mm.

6. The method according to claim 1, wherein an end of the collimator distal to the scintillator has an opening lying on the plane of a tangent to a circle having the at least one source of gamma radiation as its origin.

7. The method according to claim 1, wherein the guiding system includes a motor and a mounting part on which the at least one source of gamma radiation and the plurality of detector units are mounted, the motor being configured to cause the at least one source of gamma radiation and the plurality of detector units to rotate.

8. A method of scanning a sub-sea pipeline to detect changes in density between different parts of the sub-sea pipeline, the method comprising:
    providing at least one source of gamma radiation and a plurality of detector units configured to detect gamma radiation, each detector unit of the plurality of detector units comprising:
        i. a radiation detector comprising a scintillator comprising a scintillating material and having a detecting surface defined by its thickness t and height h, wherein t≤h at the detecting surface and having a depth d perpendicular to the detecting surface at least 2t,
        ii. a photodetector configured to detect light emitted by the scintillator in response to gamma radiation, and
        iii. a collimator disposed between the scintillator and the at least one source of gamma radiation;
    causing said at least one source of gamma radiation to emit gamma radiation along a plurality of predetermined radiation paths towards said plurality of detector units, the plurality of predetermined radiation paths passing through at least a portion of said sub-sea pipeline;
    measuring a number of photons of gamma radiation detected by each one of said plurality of detector units; and calculating a density value for each path from the number of photons of gamma radiation detected by each detector unit associated with the respective path, wherein the collimator of at least one of the plurality of detector units has a plurality of walls defining a channel with an opening, each wall of the plurality of walls being aligned with a different radius of a circle having the at least one source of gamma radiation as its origin and the opening being aligned to face directly towards the at least one source of gamma radiation.

9. A method of scanning a sub-sea pipeline to detect changes in density between different parts of the sub-sea pipeline, the method comprising:

providing at least one source of gamma radiation and a plurality of detector units configured to detect gamma radiation, each detector unit of the plurality of detector units comprising:
  i. a radiation detector comprising a scintillator comprising a scintillating material and having a detecting surface defined by its thickness t and height h, wherein t≤h at the detecting surface and having a depth d perpendicular to the detecting surface at least 2t,
  ii. a photodetector configured to detect light emitted by the scintillator in response to gamma radiation, and
  iii. a collimator disposed between the scintillator and the at least one source of gamma radiation;

causing said at least one source of gamma radiation to emit gamma radiation along a plurality of predetermined radiation paths towards said plurality of detector units, the plurality of predetermined radiation paths passing through at least a portion of said sub-sea pipeline;

measuring a number of photons of gamma radiation detected by each one of said plurality of detector units; and calculating a density value for each path from the number of photons of gamma radiation detected by each detector unit associated with the respective path, wherein providing the at least one source of gamma radiation and the plurality of detector units comprises mounting said photodetector at an angle to an axis of the collimator and the scintillator.

10. An apparatus for scanning a sub-sea pipeline to detect changes in density between different parts of the sub-sea pipeline, the apparatus comprising:

at least one source unit comprising a source of gamma radiation and shielding material configured to restrict an emission of gamma radiation from the at least one source unit;

a plurality of detector units configured to detect said gamma radiation, each said detector unit comprising:
  i. a radiation detector comprising a scintillator comprising a scintillating material and having a detecting surface defined by its thickness t and height h, wherein t≤h at the detecting surface and having a depth d perpendicular to the detecting surface at least 2t,
  ii. a photodetector configured to detect light emitted by the scintillator in response to gamma radiation, and
  iii. a collimator placed between the scintillator and the at least one source unit;

a support, said at least one source unit and said plurality of detector units being mounted on the support in a fixed spaced apart relationship;

a scanning device configured to rotate the at least one source unit and the plurality of detector units around an arc having an origin located between the at least one source unit and the plurality of detector units, the scanning device comprising a guiding system configured to guide the rotation in a predetermined path, the guiding system comprising at least two portions that are movable to form a continuous guiding system; and a data processor configured to calculate a density value for each path from photons of gamma radiation detected by each detector unit associated with the respective path.

11. The apparatus according to claim 10, wherein the plurality of detector units are arranged in close proximity to each other in the form of an arc having an origin located between the at least one source unit and the plurality of detector units.

12. The apparatus according to claim 10, wherein 1 mm≤t≤5 mm, 10 mm≤h≤50 mm, 25 mm≤d≤75 mm, and a depth of the collimator of each detector unit is in the range 50- 150 mm.

13. The apparatus according to claim 10, wherein an end of the collimator distal to the scintillator has an opening lying on the plane of a tangent to a circle having the at least one source unit as its origin.

14. The apparatus according to claim 10, wherein the guiding system includes a motor and a mounting part on which the at least one source of gamma radiation and the plurality of detector units are mounted, the motor being configured to cause the at least one source of gamma radiation and the plurality of detector units to rotate.

15. An apparatus for scanning a sub-sea pipeline to detect changes in density between different parts of the sub-sea pipeline, the apparatus comprising:

at least one source unit comprising a source of gamma radiation and shielding material configured to restrict an emission of gamma radiation from the at least one source unit;

a plurality of detector units configured to detect said gamma radiation, each said detector unit comprising:
  i. a radiation detector comprising a scintillator comprising a scintillating material and having a detecting surface defined by its thickness t and height h, wherein t≤h at the detecting surface and having a depth d perpendicular to the detecting surface at least 2t,
  ii. a photodetector configured to detect light emitted by the scintillator in response to gamma radiation, and
  iii. a collimator placed between the scintillator and the at least one source unit; and a data processor configured to calculate a density value for each path from photons of gamma radiation detected by each detector unit associated with the respective path, wherein said collimator is formed, at least in part, from a first material having a first shielding capacity for gamma radiation, and a layer of a second material, having a greater shielding capacity than the first material, and is positioned over at least one external surface of each detector unit.

16. An apparatus for scanning a sub-sea pipeline to detect changes in density between different parts of the sub-sea pipeline, the apparatus comprising:

at least one source unit comprising a source of gamma radiation and shielding material configured to restrict an emission of gamma radiation from the at least one source unit;

a plurality of detector units configured to detect said gamma radiation, each said detector unit comprising:

i. a radiation detector comprising a scintillator comprising a scintillating material and having a detecting surface defined by its thickness t and height h, wherein t≤h at the detecting surface and having a depth d perpendicular to the detecting surface at least 2t, ii. a photodetector configured to detect light emitted by the scintillator in response to gamma radiation, and iii. a collimator placed between the scintillator and the at least one source unit; and a data processor configured to calculate a density value for each path from photons of gamma radiation detected by each detector unit associated with the respective path, wherein at least one of the collimators has a plurality of walls defining a channel with an opening, each wall of the plurality of walls being aligned with a different radius of a circle having the at least one source unit as its origin and the opening being aligned to face directly towards the at least one source unit.

17. An apparatus for scanning a sub-sea pipeline to detect changes in density between different parts of the sub-sea pipeline, the apparatus comprising:

at least one source unit comprising a source of gamma radiation and shielding material configured to restrict an emission of gamma radiation from the at least one source unit;

a plurality of detector units configured to detect said gamma radiation, each said detector unit comprising:

i. a radiation detector comprising a scintillator comprising a scintillating material and having a detecting surface defined by its thickness t and height h, wherein t≤h at the detecting surface and having a depth d perpendicular to the detecting surface at least 2t, ii. a photodetector configured to detect light emitted by the scintillator in response to gamma radiation, and iii. a collimator placed between the scintillator and the at least one source unit; and a data processor configured to calculate a density value for each path from photons of gamma radiation detected by each detector unit associated with the respective path, wherein said photodetector is mounted at an angle to an axis of the collimator and the scintillator.

* * * * *